United States Patent [19]
Richerson

[11] Patent Number: 5,647,065
[45] Date of Patent: Jul. 15, 1997

[54] MALE GENITAL SUPPORTING APPARATUS AND METHOD

[76] Inventor: Michael B. Richerson, 2214 N. 28th, Tacoma, Wash. 98403

[21] Appl. No.: 633,908

[22] Filed: Apr. 17, 1996

[51] Int. Cl.$^6$ ..................................................... A41B 9/02
[52] U.S. Cl. ..................................................... 2/403; 2/227
[58] Field of Search .............................. 2/400, 402, 403, 2/113, 405, 227, 228, 238; 602/67–73

[56] References Cited

U.S. PATENT DOCUMENTS

| | | | |
|---|---|---|---|
| 898,258 | 9/1908 | Peters | 2/403 |
| 2,033,551 | 3/1936 | Rumery | 602/73 |
| 2,254,863 | 9/1941 | Weihe | 602/69 |
| 3,037,503 | 6/1962 | Ravaschieri | 2/403 |
| 3,517,666 | 6/1970 | Atlee . | |
| 3,621,846 | 11/1971 | Lehman . | |
| 4,215,685 | 8/1980 | Ibel . | |
| 4,345,337 | 8/1982 | Chung . | |
| 4,414,971 | 11/1983 | Chung . | |
| 4,660,551 | 4/1987 | Nishimura | 2/405 |
| 4,759,355 | 7/1988 | Thrower | 602/67 |
| 4,870,959 | 10/1989 | Webster . | |
| 5,029,345 | 7/1991 | Angheluta et al. . | |
| 5,070,869 | 12/1991 | Zhang . | |
| 5,133,093 | 7/1992 | Tsuchiya . | |
| 5,237,706 | 8/1993 | Nalbandian . | |
| 5,283,912 | 2/1994 | Chung | 2/403 |

Primary Examiner—C. D. Crowder
Assistant Examiner—Gloria Hale
Attorney, Agent, or Firm—William G. Forster

[57] ABSTRACT

A male supporting apparatus for supporting and lifting male genitalia. The apparatus includes a support panel for attachment to the front interior surface of a garment such as a swim suit, briefs or trousers, in front of, and adjacent to the user's genitalia. The support panel being constructed of flexible material having an adjustable aperture disposed for receiving male genitalia, including the penis and scrotum, therethrough. The aperture being adjustable in size from a first maximum circumference configuration for receiving male genitalia, to a second reduced circumference configuration to support and lift male genitalia so received. A guide conduit is incorporated in the support panel to encircle the aperture about its circumference so that a draw means/cinching cord can be slidingly received therethrough for adjusting the size of the aperture from the first configuration to the second configuration when drawn.

7 Claims, 2 Drawing Sheets

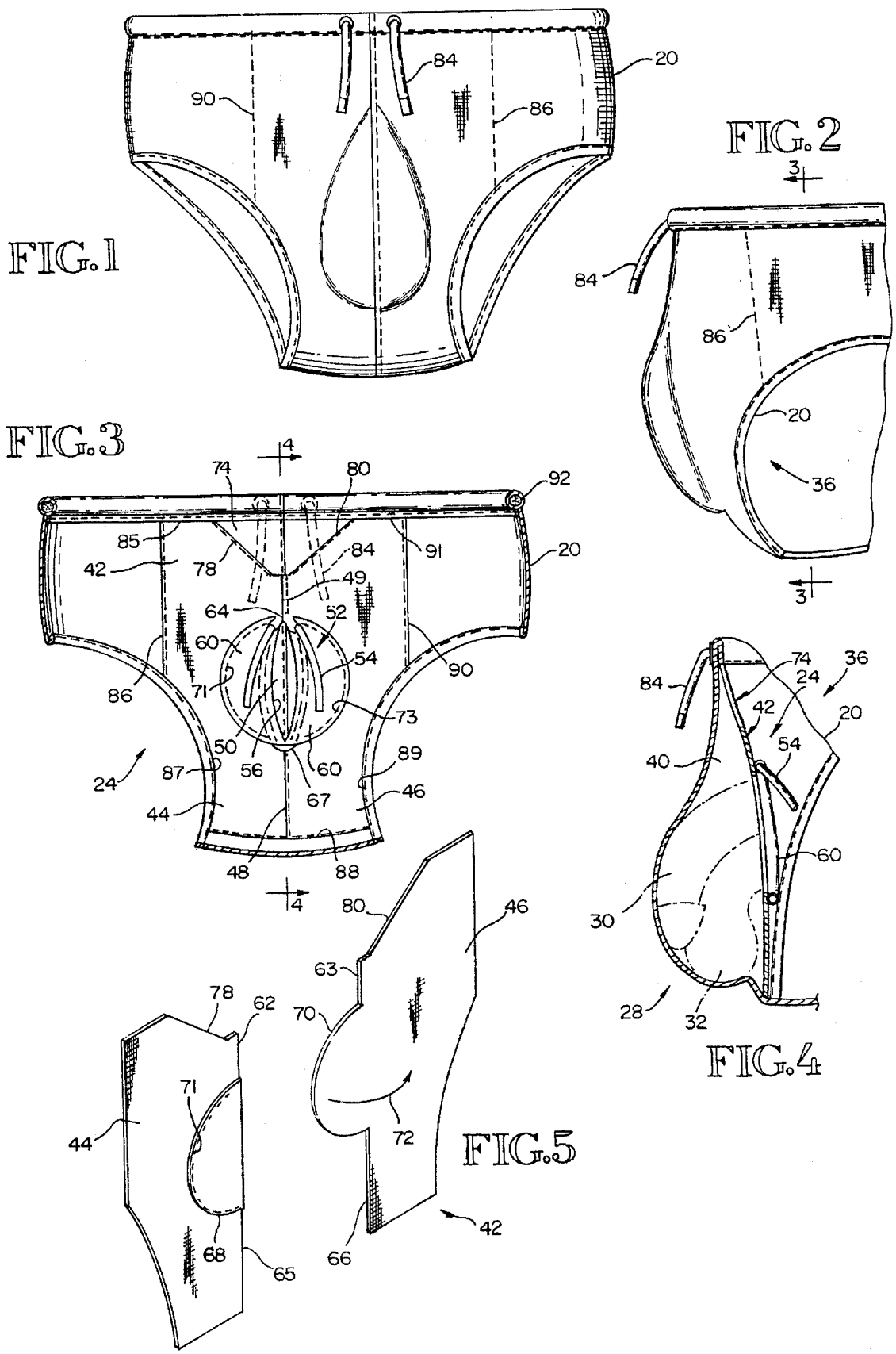

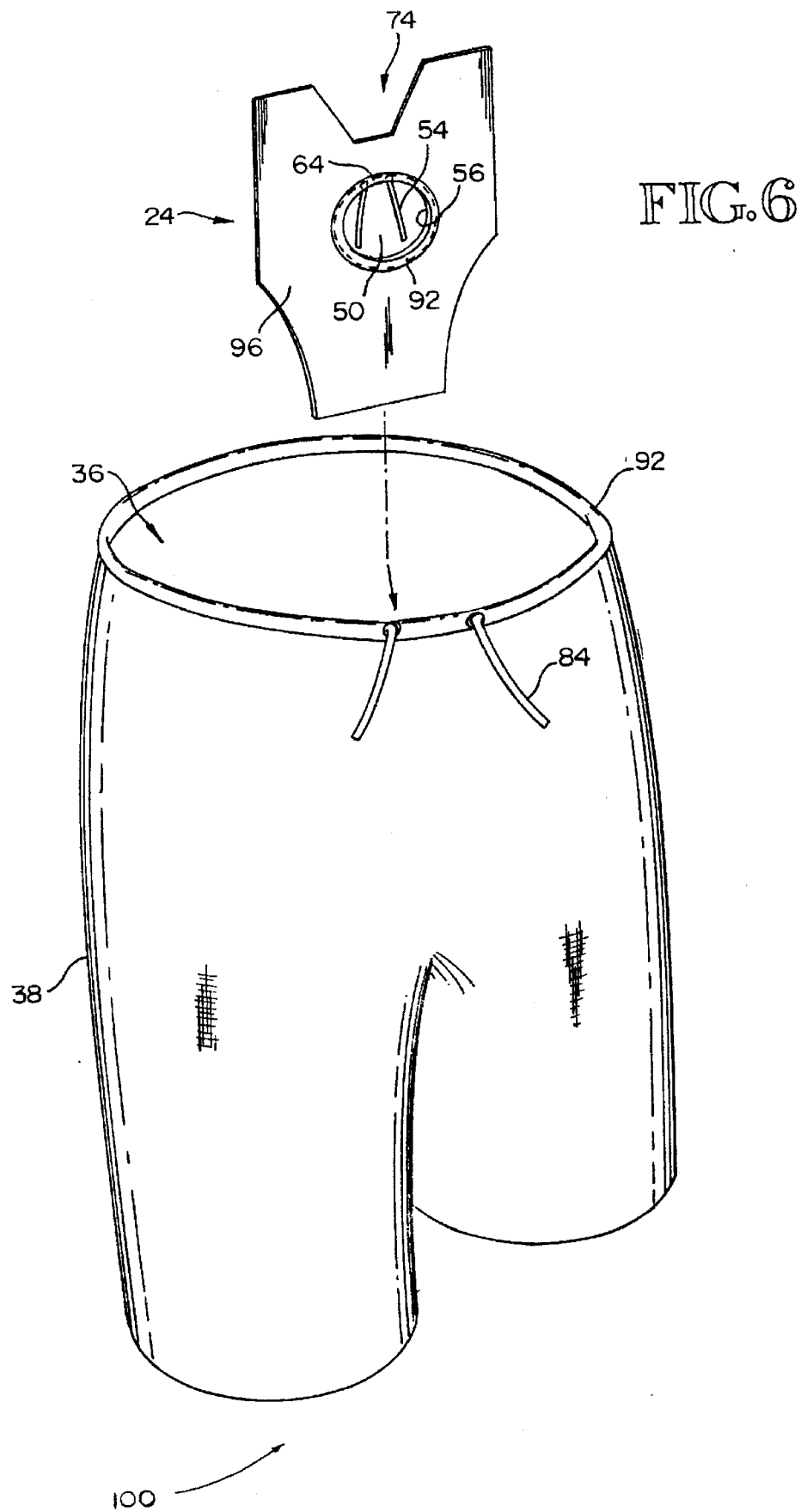

MALE GENITAL SUPPORTING APPARATUS AND METHOD

BACKGROUND

This invention relates generally to active-wear garments for males, and more particularly to garments tailored and fitted to support and lift the male genitalia up and away from the body of the user.

Garments designed and tailored specifically to accommodate male genitalia are well known in the art, and have been provided to satisfy a number of various needs including sanitation, comfort, shaping and forming, and support. In particular, many of such "male" garments are directed to problems related to sanitation and comfort. Generally, these garments are designed to either separate the whole genitalia from the body of the user, i.e., the penis and scrotum, or more commonly, to separate only the penis from the scrotum. For example, early patents including U.S. Pat. Nos. 3,621,846; 4,345,337; 4,414,971; 4,660,551; 5,029,345; 5,070,869; and 5,283,912 all provide a garment constructed to separate the penis from the scrotum of the user. Although these garments serve a particular sanitation need, they however do not address the need for a garment directed to separating the whole male genitalia from the body.

For this purpose, garments so constructed are available and include, for example, U.S. Pat. Nos. 3,517,666; 4,215,685; and 4,759,355. These garments are provided to separate the entire male genitalia from the body of the user. However, garments constructed in accordance with these patents provide little or no lifting of the genitalia up and away from the body. Moreover, such garments provide minimal individual control to adjust the same to a preferred level of support.

On the other hand, certain male garments are directed specifically to shaping, forming, and lifting the male genitalia. For example, U.S. Pat. No. 5,133,093 issued to Tsuchiya discloses a garment that includes an insert provided to shape the formation of the swell at the front of the garment. Similarly, U.S. Pat. No. 5,237,706 issued to Nalbandian discloses a male garment with a scrotal pouch designed to enable the user to displace the male genitalia from the normal position below the truck of the body to a more prominent position thus enhancing the shape thereof.

Although most of the above noted garments serve to accommodate male genitalia in one way or another, none of the same provide support to the genitatia, including the penis and scrotum, that is adjustable by the individual user to lift for comfort, and to enhance the appearance thereof.

Accordingly, a need remains for a male garment that is comfortable and easy to wear, yet can be adjusted to provide various degrees of genital lifting support according to the individual needs and desires of the user.

SUMMARY

One object of the present invention is to support and lift the male genitalia, including the penis and scrotum, to a prominent position, up and away from the body of the user.

A second object of the invention is to enhance the appearance of the user.

Another object is to increase the social confidence of the wearer.

Yet another object of the invention is to control the degree of genital support to a level preferred by the user.

A further object is to increase air circulation and ventilation around the genital area, thereby reducing body heat transmitted to the male genitalia, and increasing the comfort of the user.

Still another object is to retrofit existing garments to provide male genital support that is adjustable to the individual needs and desires of the user.

Another object is to eliminate the need for pads or inserts to enhance the appearance of the size of the male genitalia.

The invention is an improved support means for attachment to garments designed for men to be worn to assist in supporting and lifting the male genitalia of the user. The support means is retrofitted, i.e., attached inside the garment for receiving and supporting male genitalia including the penis and scrotum. The support means includes a support panel constructed of any common natural or synthetic flexible material. The support panel attaches to the interior portion of a garment, in the front thereof adjacent the region where the wearer's genitalia would naturally lie.

The attachment of the support panel to the garment is accomplished in a way that forms a pocket between the support panel and the garment. In addition, a portion of the support panel is constructed to define an aperture for receiving male genitalia therethrough, and positioning the same in the pocket formed between the garment and the support panel. The support panel includes means for adjusting the size of the aperture from a first maximum circumference configuration for receiving male genitalia, to a second reduced circumference configuration to support and lift male genitalia so received.

In accordance with one aspect of the invention the adjusting means includes a cinching cord disposed substantially about the perimeter of the aperture, the cinching cord being slidingly received by the support panel so that when the user gathers the cinching cord, the aperture adjusts to the second reduced circumference configuration. In this way, the user can control and adjust the size, i.e., perimeter of the aperture thereby setting the individual degree of support to a desired level.

In accordance with another aspect of the invention, a method is provided for supporting and lifting the genitalia of a male. The method comprises a plurality of steps including providing trousers of the type having a front interior surface disposed adjacent the wearer's genitals.

A flexible support panel is attached to the front interior surface of the trousers, adjacent the wearer's genitalia. A support panel is so attached to form a pocket between the support panel and the front portion of the trousers. Further, a portion of the support panel is tailored to define an aperture for receiving the male genitalia of the wearer including the penis and scrotum, to extend the same through the aperture to a position in the pocket formed between the garment and the support panel. The aperture is constructed to be adjustable in size from a first maximum circumference configuration for receiving male genitalia, to a second reduced circumference configuration to support and lift male genitalia so received.

Finally the method includes fitting the trousers to the wearer with the aperture being in the first maximum circumference configuration for receiving the wearer's genitals therethrough, and positioning the wearer's genitals through the aperture to a position in the pocket formed between the garment and the support panel wherein the circumference of the aperture is then adjusted to the second reduced circumference configuration.

The foregoing and other objects, features, and advantages of this invention will become more readily apparent from the following detailed description of a preferred embodiment which proceeds with reference to the accompanying drawings. Still other objects and advantages of the present invention will become readily apparent to those skilled in this art from the following detailed description, wherein the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIG. 1 is a front elevational view of a male brief garment constructed in accordance with the present invention having a support panel attached therein.

FIG. 2 is a side elevational view of a male brief garment constructed in accordance with the present invention and including a support panel attached therein.

FIG. 3 is a cross-sectional view taken along line 3—3 illustrating a support panel that includes an adjustable aperture.

FIG. 4 is a partial cross-sectional view taken along line 4—4 illustrating a support panel including a guide conduit with a cinching cord received and positioned therein, wherein phantom lines denote male genitals being received through the adjustable aperture.

FIG. 5 is a perspective view illustrating the primary flexible material components of a support panel prior to being sewn together and attached to a garment.

FIG. 6 is an exploded frontal perspective view illustrating a support panel separated from a male trouser garment that includes side portions wherein the support panel is constructed from a single piece of flexible material.

DETAILED DESCRIPTION OF PREFERRED EMBODIMENT

FIGS. 1 through 6 illustrate a male garment constructed in accordance with the present invention. Indicated generally at 20 is a male brief 20 having a supporting apparatus, i.e., support means 24 sewn therein. A support means 24 is so provided to support and lift the genitalia 28 of the user which includes the penis 30 and scrotum 32. Specifically, the support means 24 is provided to lift and separate the male genitalia 28 away from the body (not illustrated) of the wearer. Moreover, the support means 24 is provided to enhance or increase the appearance of size of the male genitalia 28.

Generally, the support means 24 is sewn to the garment in the front of the same, to interior surface 36 thereof, adjacent the region where the wearer's genitalia 28 would naturally lie, i.e., adjacent the groin. Typically, the garment is a male brief 20 or the like, including swim trunks or trousers 38 as illustrated in FIG. 6. Additionally, as will be seen in the following, the preferred embodiment of the present invention includes flexible material sections that are cut, folded and sewn together in a way to form a support panel 42 that is attached to the garment, thereby forming a pocket 40 disposed between the garment and a support panel 42. In accordance with this type of construction, any trouser or brief type of garment can be retrofitted with a support panel 42 thereby transforming the garment to one in accordance with the present invention.

Considering now in more detail, FIGS. 1–5 illustrate a preferred embodiment of the present invention. Included therein is a support means 24 defined by a support panel 42 constructed from two pieces of flexible material including a left section 44 and an adjacent corresponding right section 46 which is substantially a "mirror image" thereof. As will hereinafter be more fully described, sections 44–46 of support panel 42 are constructed and sewn together along hem lines 48 and 49. As best illustrated in FIG. 3, the sections are joined in a way to define an aperture 50 through which male genitalia 28 are received.

The aperture 50 of the support panel 42 includes an adjusting means 52 encircling the aperture 50 so that the circumference thereof can be adjusted from a maximum circumference configuration for receiving male genitalia 28, to a second reduced circumference configuration to support and lift male genitalia 28 so received. For this purpose, a cinching cord 54 is secured about the perimeter 56 of the aperture 50. The cinching cord 54 is so secured by placing the same through a guide conduit 60 which is most clearly viewed in FIGS. 3–4. More specifically, the cinching cord 54 is threaded through a cord opening 64 which is generally disposed on the upper portion of the guide conduit 60. In this way, the cinching cord 54 is slidingly received through the guide conduit 60, and can be pulled, i.e., drawn taut, wherein the circumference of the aperture 50 can be adjusted as described above.

Turning now to FIG. 5, the left section 44 and the opposing right section 46 of a support panel 42 are illustrated. Included on each section, are folding tabs 68–70. Folding tabs 68–70 are provided so that the same can be folded back and sewn to its respective section as represented by fold arrow 72 on the right section 46. As seen in FIG. 5, the right section 46 illustrates a folding tab 70 prior to being folded, and left section 44 illustrates a folding tab 68 that is folded back and sewn to its respective section along hem 71. Similarly, folding tab 70 is folded in the direction of fold arrow 72, and sewn to its respective section along hem 73 as illustrated in FIG. 3. In this way, when the right and left sections 44–66 are joined, i.e., sewn together to form a support panel 42, the folding tabs 68–70 form the guide conduit 60.

It should be noted that hem 71 of folding tab 68, and hem 73 of folding tab 70 are terminated just short of the respective upper and lower edges 62–63 and 65–66. In this way, a lower cord opening 67 is formed so that the cinching cord 54 can pass from the portion of the guide conduit 60 formed by folding tab 68 to the portion of the guide conduit 60 formed by folding tab 70. Similarly, cord opening 64 is formed on the upper portion of the guide conduit 60 to provide an entrance and exit for the cinching cord 54.

As noted above, a support panel 42 includes right and left sections 44–46 that are sewn together. In the preferred embodiment, as illustrated in FIG. 3 and FIG. 5, the sections are sewn together along their individual edges 62–63 and 65–66 which are disposed respectively above and below the folding tabs 68–70. In particular, edge 65 is sewn to edge 66 along hem line 48 (FIG. 3), from the bottom of the support panel 42 up to the guide conduit 60. Similarly, edge 62 is sewn to edge 63 along hem line 49 (FIG. 3), from the guide conduit 60 to the top of the support panel 42. Accordingly, the portion between hems 48 and 49 not sewn together, i.e., along the folding tabs 68–70, form an aperture 50 for receiving therethrough the male genitalia 28.

As previously noted, the support panel 42 is attached to the garment, in the front of the same, to the interior surface 36 thereof, e.g., man's brief 20 thereby forming a pocket 40 disposed between the garment and the support panel 42.

Because a man's genitalia 28 occupies this area, access thereto is provided through an access opening 74 so that the user can reach therethrough to adjust his genitalia 28. Access opening 74 is formed by notches 78 and 80 being formed respectively on the left and right sections 44-46, of the guide conduit 60, above hem 49. Accordingly, the support panel 42 is attached, i.e., sewn to the garment's interior surface 36 along a series of adjoining hems 85 through 91, i.e., 86, 87, 88, 89, 90, and 91, with the access opening 74 disposed on the upper portion of the support panel 42, between hem 85 and hem 91.

Turning now to FIG. 6, an alternate embodiment disclosing a one piece support panel 96 is illustrated for attachment to trousers having side leg portions 100. As can be seen, the support panel 96 includes the same primary features disclosed in the preferred embodiment including an adjustable aperture 50, a cinching cord 54 for adjusting the aperture 50, and an access opening 74. In addition, the one piece support panel 96 includes material thereof, around the aperture 50, folded and hemmed to form a guide conduit 92 through which a cinching cord 54 is slidably received. Like the preferred embodiment, the cinching cord 54 enters and exits the guide conduit 92 through a cord opening 64 disposed atop the guide conduit 92. The attachment thereof to the garment or trouser is substantially the same as in the preferred embodiment.

Considering now the method of using and wearing a garment constructed according to the present invention, a man's briefs 20 or the like are fitted with a support panel 42, which is tailored and attached to the garment as noted above. The user (not illustrated) "puts on" the garment and positions the same around his waist. Then, the user extends his genitalia 28 completely through the aperture 50. The cinching cord 54 is drawn or gathered until the proper amount of pressure is exerted to adjust the circumference of the aperture 50 to the second reduced circumference configuration, then the cinching cord is tied when the proper circumference is achieved. Finally, the user tightens a waist draw cord 84 to secure the garment about the user's waist.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

What is claimed is:

1. In a garment having a front interior surface, a support means is disposed within the garment, adjacent the front interior surface, for receiving and supporting male genitalia including the penis and scrotum, the support means comprising:

a support panel constructed of flexible material for attachment to the front interior surface of a garment adjacent the region where the wearer's genitalia would naturally lie, the attachment thereof forming a pocket between the support panel and the garment, wherein a portion of the support panel defines an aperture for receiving male genitalia, and positioning the same in the pocket formed between the garment and the support panel, the aperture being adjustable in size from a first maximum circumference configuration for receiving male genitalia, to a second reduced circumference configuration to support and lift male genitalia so received;

means for adjusting the circumference of the aperture from the first configuration to the second configuration, said adjusting means comprising a cinching cord disposed substantially about the perimeter of the aperture for adjusting the circumference of the aperture from the first configuration to the second configuration, the cinching cord being slidingly received by the support panel, wherein gathering of the cinching cord adjusts the aperture to the second reduced circumference configuration;

said support panel further comprising a guide conduit disposed about the perimeter of the aperture, wherein the guide conduit includes an opening through which the cinching cord is slidingly received to encompass the aperture's perimeter;

said support panel further comprising a left section, and an attached, corresponding right section, wherein each section further comprises a folding tab that is folded and disposed to form a portion of the guide conduit; and wherein the support panel defines an access opening disposed above the aperture, through which the wearer can reach to adjust his genitalia.

2. Support means as recited in claim 1 wherein the access opening is defined by a notch formed in the support panel.

3. In a garment having a front interior surface, a support means is disposed within the garment, adjacent the front interior surface, for receiving and supporting male genitalia including the penis and scrotum, the support means comprising:

a support panel constructed of flexible material for attachment to the front interior surface of a garment adjacent the region where the wearer's genitalia would naturally lie, the attachment thereof forming a pocket between the support panel and the garment, wherein a portion of the support panel defines an aperture for receiving male genitalia, and positioning the same in the pocket formed between the garment and the support panel, the aperture being adjustable in size from a first maximum circumference configuration for receiving male genitalia, to a second reduced circumference configuration to support and lift male genitalia so received;

means for adjusting the circumference of the aperture from the first configuration to the second configuration; and wherein the support panel is configured to define an access opening disposed above the aperture, through which the wearer can reach to adjust his genitalia.

4. Support means as recited in claim 3 wherein the access opening is defined by a notch formed in the support panel.

5. A method for supporting and lifting the genitalia of a male, the method comprising the steps:

providing trousers that include a front interior surface disposed adjacent the region where the wearer's genitals would naturally lie, attaching a flexible support panel to the front interior surface of the trousers, the attachment thereof forming a pocket between the support panel and the front interior surface of the trousers, tailoring a portion of the support panel to define an aperture for receiving the male genitalia of the wearer including the penis and scrotum, the aperture being adjustable in size from a first maximum circumference configuration for receiving male genitalia, to a second reduced circumference configuration to support and lift male genitalia so received;

fitting the trousers to the wearer with the aperture being in the first maximum circumference configuration for receiving the wearer's genitals therethrough;

positioning the wearer's genitals through the aperture to a position in the pocket formed between the garment and the support panel, adjusting the circumference of the aperture to the second reduced circumference configuration; and forming an access opening above the aperture, through which the wearer can reach to adjust his genitalia.

6. A garment designed for men to be worn to assist in supporting and lifting the male genitalia of the wearer, the garment comprising:

trousers having a front interior surface disposed adjacent the region where the wearer's genitals would naturally lie, a support panel for receiving and supporting male genitalia including the penis and scrotum, the support panel being attached to the front interior surface of the trousers, adjacent the wearer's genitalia, the attachment thereof forming a pocket between the support panel and the front interior portion of the trousers, wherein the support panel defines an aperture for receiving the male genitalia of the wearer, and locating the same to a position in the pocket formed between the front interior surface and the support panel, the aperture being adjustable in size from a first maximum circumference configuration for receiving male genitalia, to a second reduced circumference configuration to support and lift male genitalia so received;

means for adjusting the circumference of the aperture from the first configuration to the second configuration, said adjusting means comprising a cinching cord disposed substantially about the perimeter of the aperture, the cinching cord being slidingly received by the support panel, wherein gathering of the cinching cord adjusts the aperture to the second reduced circumference configuration;

said support panel further comprising a guide conduit for so receiving and positioning the cinching cord to encompass the aperture's perimeter, the guide conduit having an opening through which the cinching cord enters and exits to encompass the aperture's perimeter;

said support panel further comprising left and right sections, wherein each section defines a folding tab that folds to form a portion of the guide conduit; and wherein the support panel is configured to define an access opening disposed above the aperture, through which the wearer can reach to adjust his genitalia.

7. A garment designed for men to be worn to assist in supporting and lifting the male genitalia of the wearer, the garment comprising:

trousers having a front interior surface disposed adjacent the region where the wearer's genitals would naturally lie, a support panel for receiving and supporting male genitalia including the penis and scrotum, the support panel being attached to the front interior surface of the trousers, adjacent the wearer's genitalia, the attachment thereof forming a pocket between the support panel and the front interior portion of the trousers, wherein the support panel defines an aperture for receiving the male genitalia of the wearer, and locating the same to a position in the pocket formed between the front interior surface and the support panel, the aperture being adjustable in size from a first maximum circumference configuration for receiving male genitalia, to a second reduced circumference configuration to support and lift male genitalia so received;

means for adjusting the circumference of the aperture from the first configuration to the second configuration; and wherein the support panel is configured to define an access opening disposed above the aperture, through which the wearer can reach to adjust his genitalia.

* * * * *